United States Patent [19]

Beck et al.

[11] Patent Number: 4,834,706

[45] Date of Patent: May 30, 1989

[54] MEDICAL APPARATUS WITH A TEARABLE TAMPER EVIDENT INDICATOR MEANS

[75] Inventors: Andrew J. Beck, St. Louis, Mo.; Fredrick G. Swindler, Lakeside, Calif.

[73] Assignee: Sherwood Medical Company, St. Louis, Mo.

[21] Appl. No.: 125,032

[22] Filed: Nov. 24, 1987

[51] Int. Cl.⁴ .............................................. A61M 5/00
[52] U.S. Cl. .................................... 604/111; 604/905
[58] Field of Search ............... 604/111, 283, 326, 905; 215/203, 246; 220/264; 285/3, 4

[56] References Cited

U.S. PATENT DOCUMENTS

| | | | |
|---|---|---|---|
| 2,389,355 | 11/1945 | Goland et al. | 128/214 |
| 2,923,294 | 2/1960 | Reimann et al. | 128/214 |
| 3,305,084 | 2/1967 | Higgins et al. | 206/56 |
| 3,459,189 | 8/1969 | Alley et al. | 128/347 |
| 3,606,001 | 9/1971 | Talonn et al. | 206/63.2 |
| 3,667,781 | 6/1972 | Holbrook | 285/45 |
| 3,768,476 | 10/1973 | Raitto | 128/275 |
| 3,783,996 | 1/1974 | Gerard | 206/17.5 |
| 4,004,705 | 1/1977 | Fujio | 215/246 |
| 4,009,793 | 3/1977 | Ellsworth et al. | 215/246 |
| 4,079,738 | 3/1978 | Dunn et al. | 128/214.4 |
| 4,194,509 | 3/1980 | Pickering et al. | 604/283 |
| 4,565,293 | 1/1986 | Jonas | 215/246 |
| 4,631,056 | 12/1986 | Dye | 604/111 |
| 4,692,150 | 9/1987 | Cianci et al. | 604/111 |

*Primary Examiner*—Jerome L. Kruter
*Attorney, Agent, or Firm*—Stanley N. Garber; Andrew J. Beck; William R. O'Meara

[57] ABSTRACT

A pair of medical tube connectors are interconnected in fluid tight relation. A tamper-evident indicator of breakable material, such as paper, has a pair of strips respectively encircling said connectors, and at least one breakable strip having a width substantially less than the circumference of the tube connectors extending between the strips to provide an indication if the connectors have been separated.

20 Claims, 1 Drawing Sheet

MEDICAL APPARATUS WITH A TEARABLE TAMPER EVIDENT INDICATOR MEANS

BACKGROUND OF THE INVENTION

This invention relates to medical apparatus including fluid conduits having a tamper-evident indicator and more particularly to such apparatus wherein the tamper-evident indicator is provided at the juncture of interconnected sections of the medical fluid conduits to provide an indication that the sections have or have not been disconnected and then reconnected.

Human body fluid drainage systems, such as urine collection systems, often include a catheter, such as a Foley catheter, having its distal end disposed in the bladder of a patient and the proximal end connected to a tube connector or adaptor of a drainage tube which connects the catheter with a urine collection container or bag.

Such Foley catheters are often maintained in position in a hospitalized patient and connected to the drainage bag for substantial periods of time. To avoid patient infections, such components are usually sold in a sterile condition. However, if the components are packaged and sold separately, there is a danger of bacteria entering the urine drainage system upon assembly and connection of the catheter to the drainage tube in the field, such as in a hospital and thereby causing urinary tract infection of a patient. To avoid the possibility of bacteria entering the system at the time of connection at the juncture of the catheter and drainage tube, some manufacturers preconnect the catheter and drainage tube at the factory, sterilize the preconnected system, and package and sell the system in the assembled condition.

Certain hospital requirements necessitate the disconnection and reconnection of the catheter and drainage tube of urine collection systems such as where a replacement bag is required or bladder irrigation is desired without the removal of the original catheter from the patient. Additionally, patients sometimes are motivated to disconnect the drainage bag and tube from the catheter without authorization for reasons of patient mobility, convenience, comfort and the like. It is, of course, important to hospital personnel to know if the system connectors have been tampered with or if disconnection and reconnection of the connectors has occurred, whether or not such was for an authorized purpose. For example, when monitoring or measuring urine drainage, it is necessary to know if there has been a disconnection of the urine collection container from the catheter in order to have confidence in the determination of total amount of urine passed.

In order to provide an assured indication that the catheter has or has not been disconnected and reconnected, a tamper-evident seal has been suggested. For example, U.S. Pat. No. 4,194,509 to Pickering et al proposes a tamper-evident shrink bank or wrap which seals the juncture of the catheter and drainage tube adaptor prior to sterilization. This heat shrinkable wrap of Pickering et al consists of a length of heat shrinkable adhesive tape and a circumferentially extending tear strip made of a shrinkable resin, for example, a polyolefin such as a polyethylene. In order to apply this wrap material, a heat source must be used to shrink the wrap and this tends to complicate the overall manufacture and assembly of the system. When the tamper-evident indicator or seal of Pickering et al is in position, it conceals the juncture of the adaptor and the funnel connector of the Pickering et al device thereby making it subsequently difficult to ascertain that a proper, fluid-tight engagement exists between these elements. In order to disconnect these elements for any purpose, the tear strip of Pickering et al must be located, gripped and tangantially pulled away from the adaptor to thus remove half of the wrap from the remainder thereof and thus making removal unnecessarily complicated. Additionally, after that portion of the wrap on the adaptor of the Pickering et al device is removed with the tear strip from the remainder of the wrap of the indicator remaining on the funnel connector, it is not always apparent from the smooth band of wrap remaining that the connection between the adaptor and the funnel connector has been previously broken.

SUMMARY OF THE INVENTION

An object of the present invention is to provide a medical apparatus including a pair of conduit sections coupled together and provided with an improved tamper-evident indicator for the conduit coupling wherein one or more of the above mentioned problems or disadvantages are overcome.

Another object of the present invention is to provide an improved tamper-evident indicator for interconnected tube connectors which is easy to apply during assembly, is constructed of economical material, provides an obvious and continuing indication that the tube connectors have or have not been disconnected, and which does not interfere or complicate in any way with the disconnection of the connectors for legitimate purposes.

Still another object is to provide a unitary drainage assembly which includes a urine collection container and a urinary catheter preconnected and sterilized, and which has a tamper-evident indicator at their interconnection which is economical to make and apply, allows viewing of the interconnection of the container and catheter, provides an obvious and continuing indication of a disconnection after disconnection, and which does not substantially interfere with the disconnection of the container and catheter for a medically authorized purpose.

In accordance with one aspect of the present invention, a medical assembly is provided which includes a pair of medical conduits releasably interconnected and a tamper-evident indicator having opposed end portions each respectively encircling one of the conduits. The indicator includes a severable, axially extending portion connected between the end portions of the indicator which has a width substantially less than the circumference of the conduits.

These as well as other objects and advantages of the present invention will become apparent from the following detailed description and accompanying drawing.

DESCRIPTION OF THE PREFERRED EMBODIMENT

Figure 1:
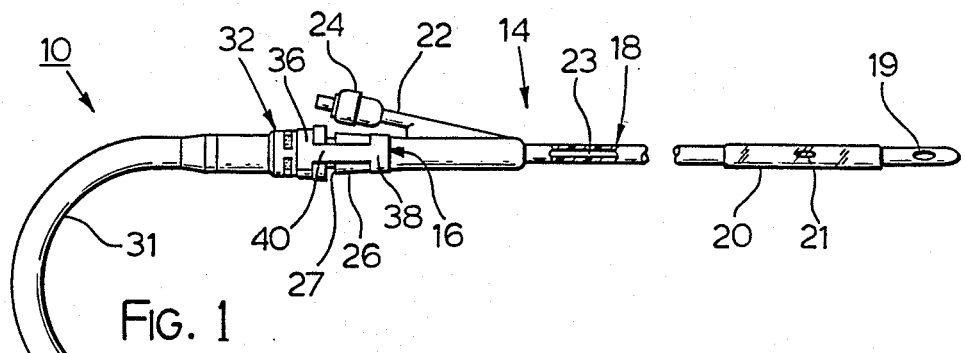
FIG. 1 is a diagrammatic illustration of a preconnected urinary drainage system, portions of which are broken away, in accordance with one embodiment of the present invention.

Referring now in more detail to the drawings, and more particularly to FIG. 1, a preconnected or closed system urinary drainage system 10 is shown including a conventional urinary drainage collection assembly 12 connected to a conventional Foley catheter assembly 14, and a tamper-evident indicator 16 at the junction of the assemblies 12 and 14 in accordance to the present invention.

Figure 2:
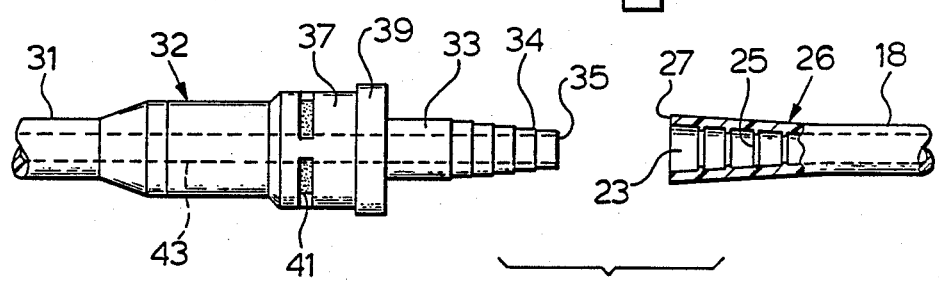
FIG. 2 is a fragmentary side view on an enlarged scale, of the drainage tube connector and the catheter connector of the system shown in FIG. 1 but shown before the tube connectors are interconnected.
Figure 3:
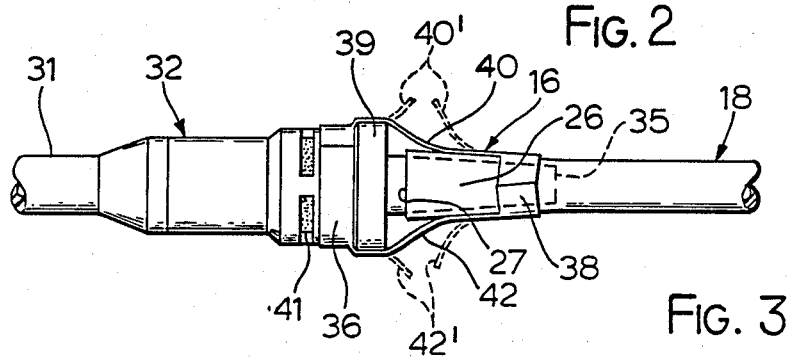
FIG. 3 is a fragmentary view of the connectors shown in FIG. 2 after they have been interconnected and after the tamper-evident indicator shown in FIG. 1 has been applied thereto.

The Foley catheter assembly 14 conventionally includes a flexible tube 18 having an inflatable balloon or cuff 20 near its distal end. The tube 18 is provided with a longitudinally extending inflation lumen (not shown) in its sidewall which is connected at its distal end to an opening 21 in the sidewall of the tube and to the interior of and between the ends of the cuff, and to an inflation tube 22 projecting in a "Y-shape" arrangement at a side of its proximal end. Inflation tube 22 has a normally closed valve 24 at the proximal end of tube 18. The valve 24 may be any suitable check valve design which can be operated by a syringe or the like for inflating and deflating the cuff in the conventional manner. One or more inlet openings 19 in the sidewall of tube 18 at the distal end connect with the main lumen, indicated at 23, of the tube 18. Tube 18 has a funnel-shaped female tube connector 26 having a longitudinal end 27 at the proximal end of the catheter assembly 14 to connect the catheter assembly to the drainage collection assembly 12. Connector 26 is shown as an integral funnel connector having tapered or conical inner and outer walls, as also seen in FIGS. 2 and 3. The inner walls of connector 26 may be provided with axially spaced friction rings 25. The catheter tube 18 and inflation tube 22 may be made of any suitable soft and flexible conventional material, for example, a material that includes silicone or latex. Such materials provide a catheter which is soft and pliable to minimize patient discomfort.

The urinary drainage collection assembly 12 is shown including a urine collection container in the form of a flexible bag 28 having an outlet 29 and a tube clamp 30 for closing and opening the outlet. A urine drainage tube 31, having a longitudinally extending drainage lumen, and which may be made of any suitable plastic such as a polyvinyl chloride, is connected at its proximal end to the interior of bag 28, and is connected at its distal end to a male or adaptor tube connector 32. The male tube connector 32, as best seen in FIG. 2, has a distal end coupling portion 33 having a tapering or generally conical outer coupling surface with a plurality of cylindrical steps decreasing in diameter in the distal direction and indicated at 34, and a longitudinal end 35 at the distal end. The coupling portion 33 is sealingly and frictionally received in the female funnel connector 26 of catheter assembly 14 to connect the distal end openings 19 of the catheter in fluid communication with the interior of collection bag 28. The steps or lands 34 cooperate with the inner surface of the inner walls and friction rings 25 in effecting a good seal between the connectors. The connector 32 also has an annular flange 39 and a cylindrical portion 37, the flange 39 being disposed axially between the cylindrical portion 37 and coupling portion 33. The diameter of flange 39 is greater than that of cylindrical portion 37 and provides a finger stop to facilitate connecting the connector 32 with funnel connector 26. Cylindrical portion 37 is of greater diameter than that of coupling portion 33. The tube connector 32 is shown having a vent with a filter at 41, and it may also include a conventional anti-reflux valve (not shown) to prevent back flow from bag 28 to the catheter 14. FIG. 2 shows the connector 32 disconnected from the funnel connector 26 and before the tamper-evident indicator 16 has been applied according to the present invention. Connector 32 has a bore or lumen indicated in phantom at 43 in FIG. 2.

After the male tube connector 32 and female funnel connector 26 have been mutually engaged and interconnected in fluid tight coupling engagement, the tamper-evident indicator 16 is positioned and connected at the juncture of the connectors as shown in FIG. 3. The indicator 16 according to the present invention includes an adaptor connecting strip 36 having a length greater than the circumference of, and adapted to be wrapped about, the cylindrical portion 37 (FIG. 2) of the male adaptor connector 32. Additionally, indicator 16 has a similar second or funnel connecting strip 38 that is adapted to be wrapped about the catheter female connector 26 and has a length greater than the circumference of that portion of the female connector 26 about which it is adapted to be wrapped. A pair of transversely circumferentially spaced severable, tearable or breakable indicator strips 40 and 42 are connected between the connecting strips 36 and 38. While two indicator strips 40 and 42 are shown in the drawing one such strip is generally sufficient.

Figure 4:
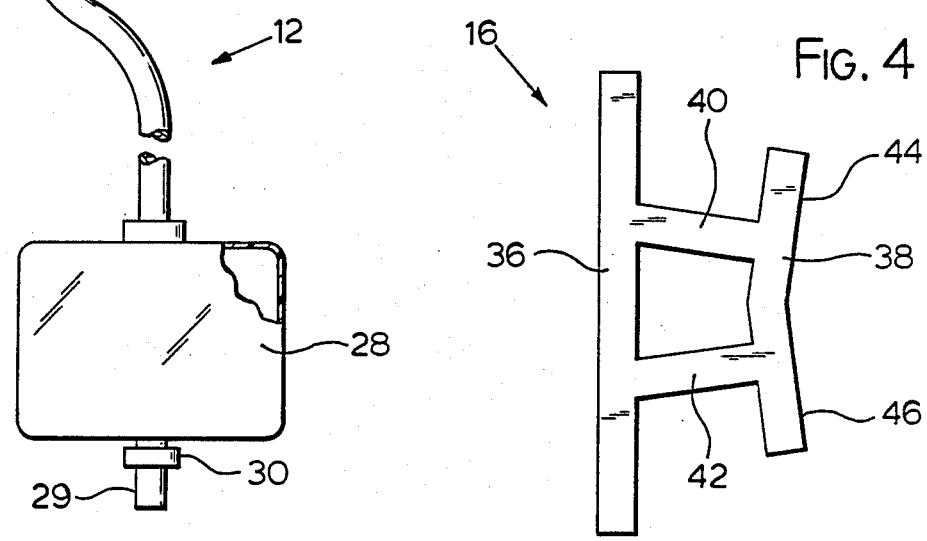
FIG. 4 is a plan view of a tamper-evident indicator shown in FIG. 3 but shown in a flattened condition, as before being applied to the remainder of the system shown in FIG. 1.

The indicator 16 is shown in FIG. 4 as a unitary or single piece member and in its manufactured and flattened state. It is formed of an easily tearable paper, preferably with an adhesive (not shown) applied at least to end portions of the connecting strips and may be applied to the entire one side of the connecting strips of the indicator. The connecting strip 36 is shown in FIG. 4 extending vertically and having upper and lower ends, which ends overlap when applied to the cylindrical portion 37 of the connector 32, as shown in FIG. 3. The overlapping ends are connected together by the adhesive. The funnel connecting strip 38 is shorter than the adaptor connecting strip 36 because the circumference of the funnel at the strip mounting point is less than the circumference of the adaptor connector at portion 37. The connecting strip 38 is shown having an upper portion 44 extending at a slight angle, such as 8° from a vertical line, and inclined toward the connecting strip 36. Similarly, a lower portion 46 of connecting strip 38 connects with portion 44 and also extends at an angle, for example, 8° from a vertical line and toward the connecting strip 36. Portions 44 and 46 connect at a point on a horizontal line intersecting the center of connecting strip 36. The axially or transversely extending indicator strips 40 and 42 extend from connecting strip 36 at locations spaced from the opposite ends of strip 36 and rightwardly at an angle, for example, 8° from a horizontal line with each inclined toward each other in the direction of strip 38. By forming the indicator strips 40 and 42 spaced from each other and parts of the indicator 16 at angles, as described herein, the connecting strip 38 will be readily wrapped around the relatively smaller circumference of the catheter connector 26 with the opposed ends thereof overlapping each other and connected together by the adhesive while remaining parallel to the longitudinal axis of the connectors and without crinkling. While the connecting strip 38 has portions at angles to a vertical line, depending on the relative circumferences of the connectors, both strips may be made straight and vertical like connecting strip 36 and the tearable or breakable indicator strips 40 and 42 may be made horizontal or normal to the longer axis of the connecting strip 36.

When the indicator 16 is applied to the tube connectors 26 and 32, the indicator strips 40 and 42 will extend longitudinally or axially across the juncture of the connectors 26 and 32 and be diametrically spaced from each other. Such strips will not be wrapped about or entirely conceal the juncture. After the indicator 16 has been applied at the juncture of the connectors 26 and 32, the entire assembly 10 may then be sterilized and packaged.

The tamper-evident indicator 16 may be stamped out of a suitable paper in the form shown in FIG. 4, which paper may be any suitable severable or tearable paper such as conventional wood pulp paper or the like, and may either be coated with a wetable-and-subsequently-hardening glue for attaching it to the tube connectors 26 and 32 or it may be of a pressure sensitive adhesive of the type in which a protective sheet of material (not shown) is peeled away to present one side of the material with an adhesive that does not harden and that can be applied directly to the connectors without wetting. One side of indicator 16 may be entirely coated with adhesive or only one of the overlapping ends of each of the connecting strips 36 and 38 may be adhesively coated. If desired, only the encircling connecting portions 36 and 38 may be coated with an adhesive. With the opposite ends of each of the connecting strips 36 and 38 overlapping and adhesively connected together it is not necessary that these strips be adhesively connected to both tube connectors 26 and 32. For example, where the catheter 18 is of silicone, some adhesives will not tightly adhere to the catheter, however, the ends of connecting strip 38 overlap and are tightly adhesively connected together so that strip 38 is tightly connected to connector 26. Some adhesives provide only a tackiness with silicone.

Should it be desired to disconnect the connectors 26 and 32 from each other, the indicator strips 40 and 42 will readily tear or become broken. Upon tearing, the torn ends of the indicator strips may curl outwardly, as shown in phantom lines at 40' and 42' in FIG. 3, thereby making it obvious, even to the casual observer, that the connection has been broken. While two indicator strips or more are desirable, one can be used. Where the connectors are completely disconnected from each other, both of the indicator strips 40 and 42 will be broken while the connecting strips 36 and 38 will remain secured on the connectors 26 and 32. Even if the connectors were reconnected after a disconnection, the presence of curled, or uneven remnant torn indicator strips would be a clear indication that the connectors had been disconnected.

Since the indicator strips 40 and 42 are relatively narrow, substantially less than the circumference of the connectors 26 and 32, the juncture of the connectors 26 and 32, including the distal side of flange 33, surface 34 and funnel connector end 27, can be seen between the indicator strips when desired so that the indicator strips need not be transparent but can be of any desired color and still not conceal the connector junction. The proximal end 27 of the conical connector 26 provides a junction line at the juncture of connectors 26 and 32. Also, since the indicator strips 40 and 42 are easily torn or broken, the indicator does not interfere with, hinder, or complicate the disconnection of the connectors 26 and 32.

As various changes could be made in the above construction without departing from scope of the invention, it is intended that all matter contained in the above description and shown in the accompanying drawing be interpreted as illustrative and not in a limiting sense.

What is claimed is:

1. A medical apparatus comprising a pair of medical conduits, each of said conduit having a longitudinal axis and releasably connected together at a junction line formed at one end of one of said conduits, and a separate tamper-evident indicator including first and second portions, said portions respectively encircling said conduits remote from said junction line, and a third portion of tearable material connected to and extending longitudinally between said first and second portions, said third portion having a width less than the circumference of each of said conduits to permit direct viewing of said junction line and being tearable and severable in response to predetermined relative movement between said conduit to provide an indication if said movement occurs.

2. The assembly of claim 1 wherein said indicator is a single-piece of paper.

3. The assembly of claim 2 wherein said first and second portions of said indicator comprise strips having lengths greater than the circumference of each of said conduits which they respectively encircle, and said third portion includes a pair of spaced indicator strips connecting said strips of said first and second portions together.

4. The assembly of claim 3 wherein said strip of said first portion has a greater length than that of said strip of said second portion, and said pair of spaced indicator strips are in non-parallel relation to each other and spaced closer together where they connect with strip of said second portion.

5. A medical assembly comprising a pair of flexible medical tubes, a pair of tube connectors respectively connected to said tubes and releasably connected together to connect said tubes in fluid communication with each other, and a separate tamper-evident indicator including first and second portions respectively encircling said connectors to respectively connect the opposed end of said indicator to said connectors, and a third portion integrally connected to and extending longitudinally between said first and second portions, said third portion having a width less than the circumference of said connectors and being tearable and severable in response to predetermined relative longitudinal movement between said connectors to provide a visual indication if disconnection of said tubes has occurred.

6. The assembly of claim 5 wherein said third portion is of tearable paper.

7. The assembly of claim 6 including an adhesive on at least one of the opposed longitudinal ends of each of said first and second portions, the opposed ends of each of said first and second portions overlap of each other with the ends fixed together by said adhesive.

8. The assembly of claim 7 wherein all of said portions are of tearable paper.

9. The assembly of claim 8 wherein all of said portions are integrally connected together.

10. The assembly of claim 7 wherein said indicator is a single-piece of paper and includes a fourth portion having a width less than the circumference of said connectors and is diametrically spaced from said third portion and severable upon said predetermined movement.

11. The assembly of claim 8 wherein one entire side of each of said first and second portions are covered by said adhesive.

12. The assembly of claim 11 wherein one entire side of said indicator is covered by said adhesive.

13. A urine collection assembly comprising a urine collection container, a drainage tube having a lumen extending therethrough and connected at the proximal end to said container, a first tube connector connected to the distal end of said tube and having a lumen extending therethrough, said first tube connector including a tapering longitudinally extending end connector portion, and a cylindrical portion proximally of said connector portion and having a diameter greater than said end connector portion, a catheter having a distal end for insertion into the bladder of a patient, a second tube connector integrally connected to the proximal end of said catheter and having inner and outer generally conical walls and a proximal end, said tube connectors being releasably connected together with said end portion of said first connector telescopically received in said second connector in fluid tight engagement with the overlapping inner conical walls of said second connector to connect said drainage tube and said catheter in fluid communication with each other, and a separte tamper-evident indicator including a pair of longitudinally spaced connecting strips encircling and connected respectively to said cylindrical portion of said first connector and said outer wall of said second connector, said connecting strips being remote from said proximal end of said second connector, and a longitudinally extending severable indicator strip connected to and extending between said connecting strips and being tearable and breakable in response to predetermined movement between said connectors to provide a visual indication if said movement occurs, said indicator strip having a width less than the circumference of said connectors to expose said proximal end of said second connector to view.

14. The assembly of claim 13 wherein each of said connecting strips extends more than 360° around the connector it encircles so that one end portion thereof overlaps the opposite end portion thereof, said one end portion of each of said connecting strips being adhesively connected to its opposite end portion.

15. The assembly of claim 14 wherein said indicator strip is of paper.

16. The assembly of claim 14 wherein said indicator is a single piece of paper.

17. The assembly of claim 14 wherein one entire side of said indicator has an adhesive thereon.

18. The asembly of claim 13 wherein said indicator includes a second longitudinally severable indicator strip integrally connected to and extending between said connecting strips and circumferentially spaced from said first named severable indicator strip.

19. The assembly of claim 13 wherein said first tube connector has a radially extending flange between said end connector portion and said cylindrical portion which is exposed to view.

20. The assembly of claim 13 wherein said indicator is a single-piece of paper.

* * * * *